(12) United States Patent
Kriger

(10) Patent No.: US 6,816,807 B2
(45) Date of Patent: Nov. 9, 2004

(54) HIDDEN OVERWEIGHT PREVENTING SYSTEM AND METHOD

(76) Inventor: Yefim G. Kriger, 445 Beaver St., Ansonia, CT (US) 06401

( * ) Notice: Subject to any disclaimer, the term of this patent is extended or adjusted under 35 U.S.C. 154(b) by 0 days.

(21) Appl. No.: 10/349,720

(22) Filed: Jan. 23, 2003

(65) Prior Publication Data

US 2004/0148127 A1 Jul. 29, 2004

(51) Int. Cl.$^7$ ............................................. G06F 15/02
(52) U.S. Cl. ...................................... 702/173; 600/300
(58) Field of Search ......................... 702/173; 600/300, 600/301; 174/113 R; 177/25.13; 705/3

(56) References Cited

U.S. PATENT DOCUMENTS

| | | | |
|---|---|---|---|
| 3,808,694 A | 5/1974 | Hutchinson et al. | 33/169 R |
| 4,237,344 A | 12/1980 | Moore | 179/2 A |
| 4,318,447 A | 3/1982 | Northcutt | 177/25 |
| 4,366,873 A | 1/1983 | Levy et al. | 177/25 |
| 4,423,792 A | 1/1984 | Cowan | 177/25 |
| 4,576,244 A | 3/1986 | Zeigner et al. | 177/245 |
| 4,602,280 A | 7/1986 | Maloomian | 358/93 |
| 4,629,015 A | 12/1986 | Fried et al. | 177/25 |
| 4,686,624 A | 8/1987 | Blum et al. | 364/415 |
| 4,796,182 A | 1/1989 | Duboff | 364/413.29 |
| 4,951,197 A | 8/1990 | Mellinger | 364/413.2 |
| 5,014,298 A | 5/1991 | Katz | 379/93 |
| 5,023,901 A | 6/1991 | Sloan et al. | 379/38 |
| 5,127,003 A | 6/1992 | Doll, Jr. et al. | 370/110.1 |
| 5,142,484 A | 8/1992 | Kaufman et al. | 222/638 |
| 5,170,426 A | 12/1992 | D'Alessio et al. | 379/38 |
| 5,218,344 A | 6/1993 | Ricketts | 340/573 |
| 5,412,564 A | 5/1995 | Ecer | 364/413.29 |
| 5,542,420 A * | 8/1996 | Goldman et al. | 600/301 |
| 5,596,994 A | 1/1997 | Bro | 128/732 |
| 5,673,691 A | 10/1997 | Abrams et al. | 128/630 |
| 5,704,350 A | 1/1998 | Williams, III | 128/630 |
| 5,722,418 A | 3/1998 | Bro | 128/732 |
| 5,763,837 A * | 6/1998 | Davignon et al. | 174/113 R |
| 5,774,871 A | 6/1998 | Ferro | 705/15 |
| 5,796,640 A | 8/1998 | Sugarman et al. | 364/709.02 |
| 5,839,901 A | 11/1998 | Karkanen | 434/127 |
| 5,857,967 A | 1/1999 | Frid et al. | 600/301 |
| 5,876,926 A | 3/1999 | Beecham | 435/5 |
| 5,878,746 A | 3/1999 | Lemelson et al. | 128/653.1 |
| 5,892,856 A | 4/1999 | Cooper et al. | 382/291 |
| 5,908,301 A | 6/1999 | Lutz | 434/236 |
| 5,933,136 A | 8/1999 | Brown | 345/327 |
| 5,937,387 A | 8/1999 | Summerell et al. | 705/2 |
| 5,941,825 A | 8/1999 | Lang et al. | 600/449 |
| 5,945,107 A | 8/1999 | Hessel et al. | 424/195.1 |
| 5,946,659 A | 8/1999 | Lancelot et al. | 705/3 |
| 5,954,640 A | 9/1999 | Szabo | 600/300 |
| 5,967,789 A | 10/1999 | Segel et al. | 434/236 |
| 6,022,315 A | 2/2000 | Iliff | 600/300 |
| 6,032,084 A | 2/2000 | Anderson et al. | 700/241 |
| 6,032,120 A | 2/2000 | Rock et al. | 705/2 |
| 6,083,006 A | 7/2000 | Coffman | 434/127 |
| 6,097,927 A | 8/2000 | LaDue | 434/308 |
| 6,153,409 A | 11/2000 | Bentley et al. | 435/69.7 |
| 6,157,337 A | 12/2000 | Sato | 341/155 |
| 6,168,563 B1 | 1/2001 | Brown | 600/301 |
| 6,190,313 B1 | 2/2001 | Hinkle | 600/300 |
| 6,199,099 B1 | 3/2001 | Gershman et al. | 709/203 |
| 6,246,967 B1 | 6/2001 | Libicki et al. | 702/101 |
| 6,322,504 B1 * | 11/2001 | Kirshner | 600/300 |
| 6,336,136 B1 | 1/2002 | Harris | 709/219 |
| 6,369,337 B1 * | 4/2002 | Machiyama et al. | 177/25.13 |
| 2003/0158756 A1 * | 8/2003 | Abramson | 705/3 |

* cited by examiner

Primary Examiner—John Barlow
Assistant Examiner—Xiuqin Sun
(74) Attorney, Agent, or Firm—Cantor Colburn LLP; Christopher C Boehm

(57) ABSTRACT

A method and apparatus for preventing an overweight condition by monitoring the weight of individuals before they will become overweight, the apparatus and related systems analyze the data and provides a warning of if the existence of an overweight trend is found.

19 Claims, 11 Drawing Sheets

HIDDEN OVERWEIGHT PREVENTING SYSTEM AND METHOD

FIELD OF INVENTION

This invention relates to health care method and system that prevents overweight conditions in children and adults by long term monitoring of their weight progress and predicting the occurrence of an overweight condition.

BACKGROUND

There are many types of weight control systems and methods. Many weight control plans are available to individual users from which the user can select a particular program designed to control the weight of the individual.

Numerous patents are directed to different types of health care systems, some examples are provided below: U.S. Pat. Nos. 3,808,694; 4,237,344; 4,318,447; 4,366,873; 4,423,792; 4,576,244; 5,014,298; 5,023,901; 5,127,003; 5,142,484; 5,170,426; 5,218,344; 5,412,564; 5,596,994; 5,704,350; and 6,336,136.

For the correct correlating weights of individuals of different age, gender, and height with respective to weight control diet plans, recommendations of the following book: Bowes and Church's Food Values of Portions Commonly Used 15th edition revised by Jean A. T. Pennington, Ph.D., R. D. Harper & Row, Publishers, New York, 1989, are available.

Despite the methods and apparatus mentioned above many adult Americans and children are still overweight. It seams that these poor results are due to the fact that overweight people tend to consult doctors after they became overweight instead of before the condition occurs. Once a person is overweight it is often more difficult to treat the condition.

SUMMARY

The present disclosure relates to the general field of information services, education, and personal heath care and more particularly, a computerized nondialog system that conveys one-way health awareness messages and maintains surveillance of a user by hidden monitoring weight and height information. The present disclosure uses a network service which provides feedback warnings to a client's primary doctor to increase or maintain healthy changes over a period of time and comprises means for measuring and recording a client's weight and height and transmitting this information by e.g., internet, wireless communication or other data transfer means for use in a overweight preventing program.

A method and system for preventing an overweight condition in an individual by using a device to remotely monitor the weight of the individual and providing that information to a remote system in order to predict an overweight trend and take the necessary steps (e.g., dieting prior to the overweight condition) in order to curtail the overweight condition from occurring.

One aspect of the present disclosure is to provide a Hidden Overweight Preventing System (HOPS) that identifies the first signs of an overweight condition in a monitored individual. The system prevents the overweight condition from occurring by monitoring an individual's weight periodically before they become overweight. Accordingly, the monitoring and analyzing means will provide a warning to the individual's primary doctor of an overweight condition and it will be much easier to for the individual's doctor to treat the overweight condition.

More particularly, the instant apparatus and method provides a very quick reading of the weight and occasionally (once in a month) the height of the individual before he or she goes to bed.

Furthermore, this system utilizes a measuring means whose power is turned off and activated by the individual automatically when he or she steps onto the platform of the power-controlled weight and height measuring devices.

Another object of the present disclosure is to provide a more reliable overweight preventing system, which is also convenient to the individual or user. The device and method of the present disclosure employs an automatic analyzer of the weight progress of an individual in order to create a trend of the individual's weight progress (either upward, downward or the same) and send a warning about signs of an overweight condition or abrupt weight loss to the individual's primary doctor. By using trending predictions the doctor will be able to predict an overweight condition several months before it will occur.

When the first signs of overweight condition or trend are observed or predicted, the apparatus of the present disclose allows the individual to choose a diet plan and exercises from a plurality of diet plans and exercises in the memory of a personal computer that can be connected to the system.

DETALED DESCRIPTION

Figure 1:
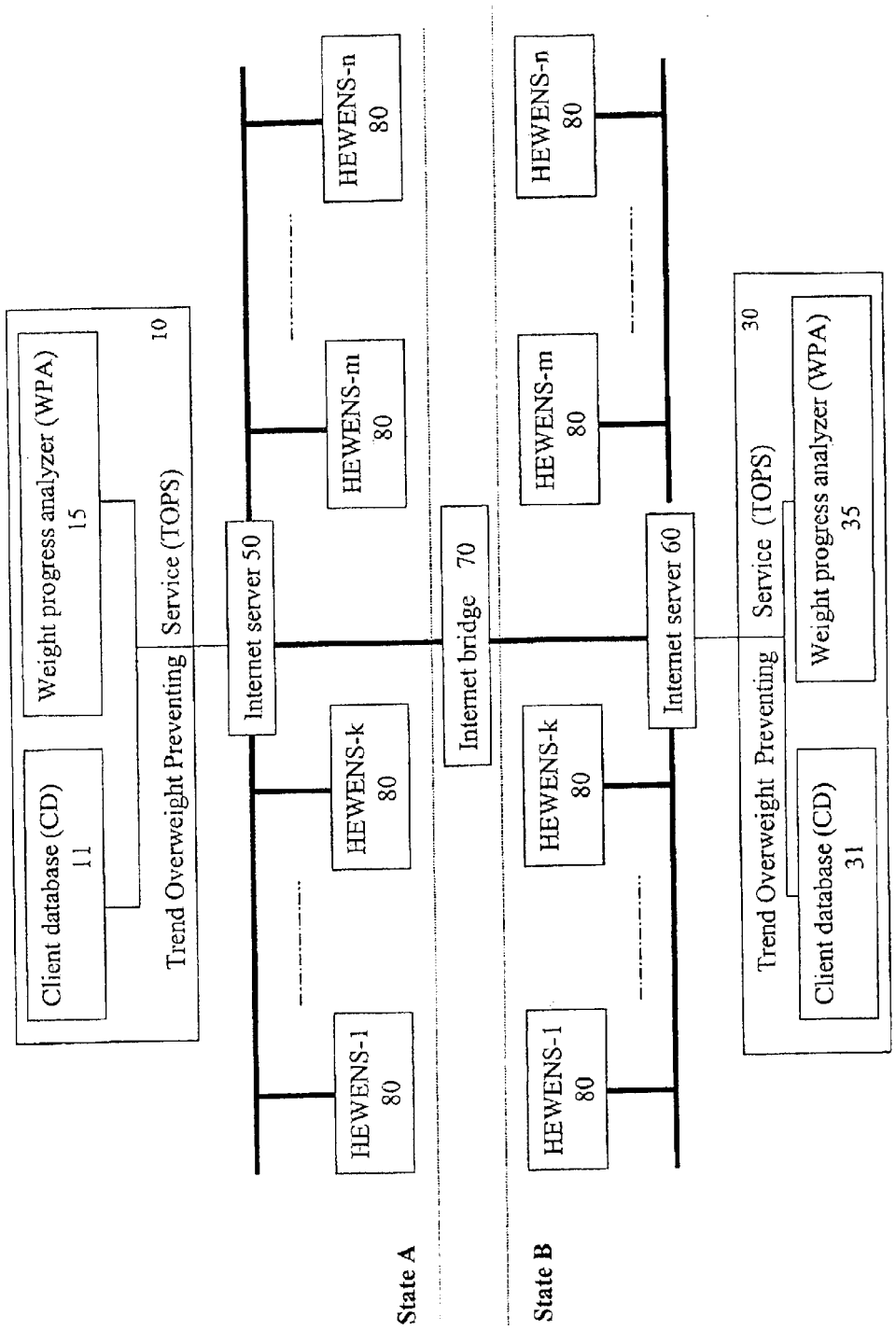
FIG. 1 is a schematic display of a hidden overweight preventing system structure.

FIG. 1 shows a block diagram of the hidden overweight preventing system (HOPS) according to an exemplary embodiment of the present disclosure. The HOPS system comprises a plurality of apparatus for collection and a one-way automatic data transmission (via data transfer means, e.g., internet or wireless communications, etc.) to a main data bus or system. The apparatus are capable of being packaged in a convenient power-controlled weight and height measuring device and adapted to interface with a main system for automatic data transfer.

The system comprises of a trend overweight preventing service (TOPS) 10 that is personal computer (PC) based and interacts with another system, which may be a government or private company located in remote locations. For example, in FIG. 1 TOPS 10 is located in state A of a country. The goal of this service is to collect the weight and height data automatically received from patients through a plurality of Height and Weight News Senders devices 80 (HEWENS) using a data transfer means such as an internet server 50 configured to receive and disperse the collected information. The HEWENS device is an automatic device that is triggered or activated by an individual when he/she steps on a weight and height measuring platform. After the required measurements (weight and height) have completed, the HEWENS device automatically sends the collected data to the TOPS system through a data transmission medium such as the Internet. The HEWENS devices can be purchased by individual users or they can be prescribed by doctor's participating in the HOPS system.

Once the information is received and analyzed by the TOPS system, an appropriate warning is issued to an individual's primary doctor if an overweight condition is predicted. TOPS 10 consists of a client database (CD) 11 and weight progress analyzer (WPA) 15. The client database automatically collects the name, age, sex, weight, height, and physical type of the patient through HEWENS devices 80 through Internet server 50. The weight progress analyzer 15 has in its memory a doctor's recommended weight for the patient depending on age, sex, height, and physical type of the patient.

In addition, it is also contemplated that the TOPS system may be a subscriber network wherein users of the HEWENS devices are able to log onto the system for a pre-determined monitoring fee.

Analyzer 15 receives the current weight of the patient from the client database 11 and creates a graph of the patient's weight progress using known statistical methods and compares it to a recommended one. The analyzer 15 will then determine if the individual is trending towards an overweight condition by employing a computer algorithm for comparing received data towards recommended data, trends or graphs. If the analyzer 15 discovers that the person will be overweight in several months in the future, if the current trend continues, the system sends a warning message (by e-mail or by a phone) to a primary doctor of the patient. Thus, the primary doctor starts to contact the patient directly by phone and explain the reason why the doctor is calling, and accordingly makes an appointment. After the doctor conducts a physical, he discovers the reason of the potential overweight condition and may suggest to the patient a treatment or several different diet plans and exercises or give a referral to the dietitian or nutrition specialists. Accordingly, the system of the present disclosure is able to assist in getting the individual into contact with the doctor prior to the existence of an overweight condition.

FIG. 1 shows also a structure of another state (state B) or region of the trend overweight preventing service for a country. The trend overweight preventing service (TOPS) 30 of the state B similarly to state A consists of a client database (CD) 31 and a weight progress analyzer (WPA) 35. The client database automatically collects the name, age, sex, weight, physical type, and height of the patient through a plurality of HEWENS devices 80 of this region and Internet by the Internet server 60. The weight progress analyzer 35 has in its memory the doctor's recommended weight for the patient depending on the age, sex, height and physical type of the patient. Analyzer 35 obtains the current weight of the patient from the client database 31 and creates a graph of the patient's weight progress and compares it to the recommended one. If the analyzer 35 by use of comparison algorithms discovers that the person will be overweight in several months if the current trend continues, it sends a warning message (by e-mail or by a phone) to a primary doctor of the patient. The primary doctor starts to contact a patient directly by the phone, explain the reason why the doctor is calling, and makes an appointment. After the doctor asked the patient to do some tests, he discovers the reason of the potential overweight and may suggest to the patient a treatment or several different diet plans and exercises or give a referral to the dietitian or nutrition The internet server 50 of the state A and internet server 60 of the state B are connected to each other by internet bridge 70. In addition, the system can also be configured to report significant weight losses, which may be attributable to an illness wherein a message will also be sent to the individual's primary physician.

In addition, the TOPS system of state A can communicate with state B via internet servers 50 and 60 and internet bridge 70 in order to create Federal or National long term overweight preventing service.

Figure 2:
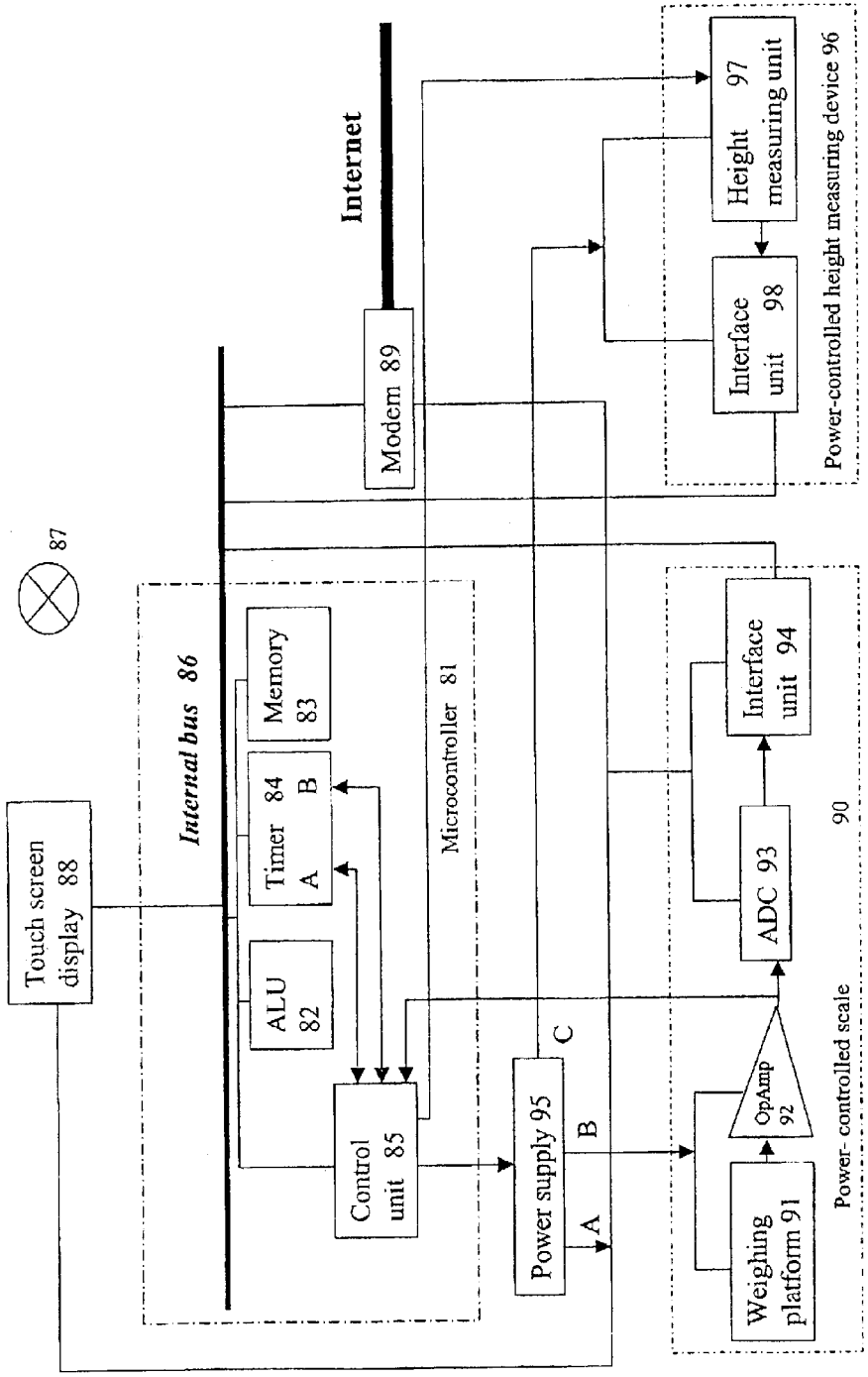
FIG. 2 is a block diagram of a height and weight news sender.

FIG. 2 shows a block diagram of the Height and Weight News Sender (HEWENS) 80 that consists of a microcontroller 81, touch screen display 88, modem 89, power-controlled scale 90, voltage-controlled power supply 95, and power-controlled height measuring device 96. The following description is related to a touch screen type of a display-keyboard unit 88. Microcontroller 81, in turn, consists of an arithmetic-logic unit 82, memory 83, timer 84, control unit 85, and internal bus 86. Each manufactured HEWENS 80 has it's own internet address and internet address and name of the trend overweight preventing service (TOPS) server for communication via internet.

When the owner or user of the HEWENS unit, who appears to be a potential patient, powers up the HEWENS unit for the first time at home, the touch screen display 88, modem 89, power-controlled scale 90, and power-controlled height measuring device 96 will be supplied by the voltage supply 95 through it's terminals A, B, and C. Voltage supply 95 may be battery powered or a direct AC connection.

Figure 3:
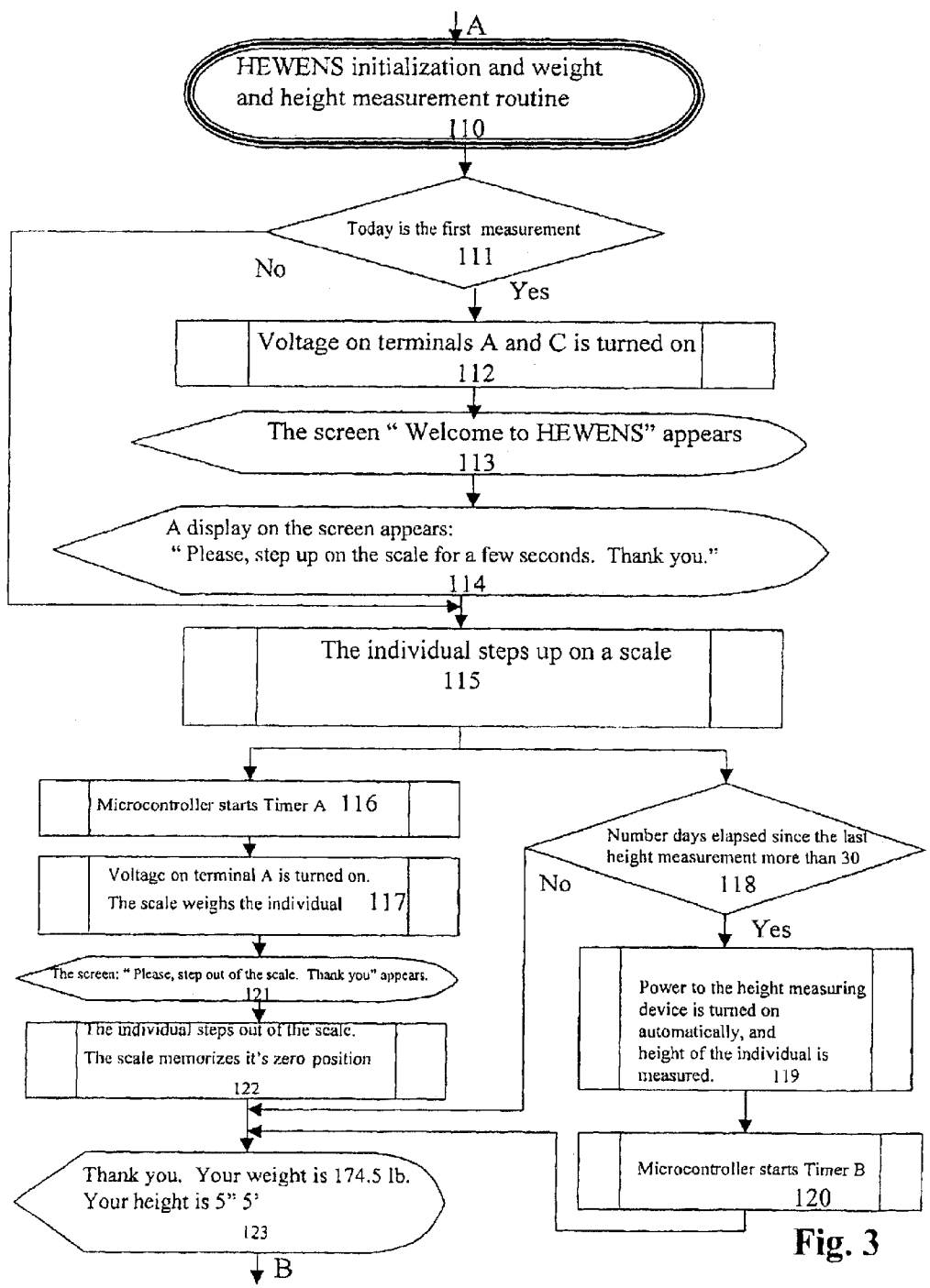
FIG. 3 is a flowchart for the HEWENS initialization and weight and height measurement routine.

FIG. 3 shows a HEWENS device initialization and weight and height measurement routine 110, which is run when the system is powered up for the first time or reset. Routine 110 is resident upon the microprocessor of the device. When the device is turned on for the first time at decision node 111 the voltage on terminals A and C is turned on (block 112), and the phrase "Welcome to the HEWENS" appears (block 113). In addition, a short presentation of the hidden overweight preventing system (HOPS) is viewed by the user. This can be stored in the read only memory (ROM) of the device. Next, an invitation to the patient to step up on the scale platform appears (block 114). It is preferred in order to obtain the best results to measure weight and height at the same time every day (e.g., night when a patient goes to bed with minimal clothes on). After a patient steps upon the platform (block 115), a control unit 85 recognizes the operator on the scale by receiving a signal of the operational amplifier circuit 92, which is outputted when an individual steps on the scale. Microcontroller 81 through a control unit 85 starts timer A (block 116) that will give an output signal when 30 minutes elapse. Of course, other time ranges can be programmed into the unit. After that the scale weighs the patient (block 117) the phrase "Please, step off of the scale. Thank you" appears on the screen (block 121). After the individual steps out off the weighing platform, the scale memorizes its zero position (block 122).

As an alternative the device is equipped with a display or non-display option. In the non-display option the screen of the weighing device will not provide any messages to the user and will operate in a stealth mode wherein the user in not aware of the operation of the device nor does the user see the weight readings.

Simultaneously, microcontroller 81 will check an output of the timer B that counts the number of days elapsed after a previous measurement (decision node 118) of the last height reading of the patient. Every time when the output of timer B is active (it means that 30 days or more elapsed since the previous height measurement), terminal C of the power supply will be turned on and height of the patient will be measured (block 119). Microprocessor will start timer B (block 120) to count the next 30 days. The touch screen will also show the weight and height of the patient (block 123).

Figure 4:
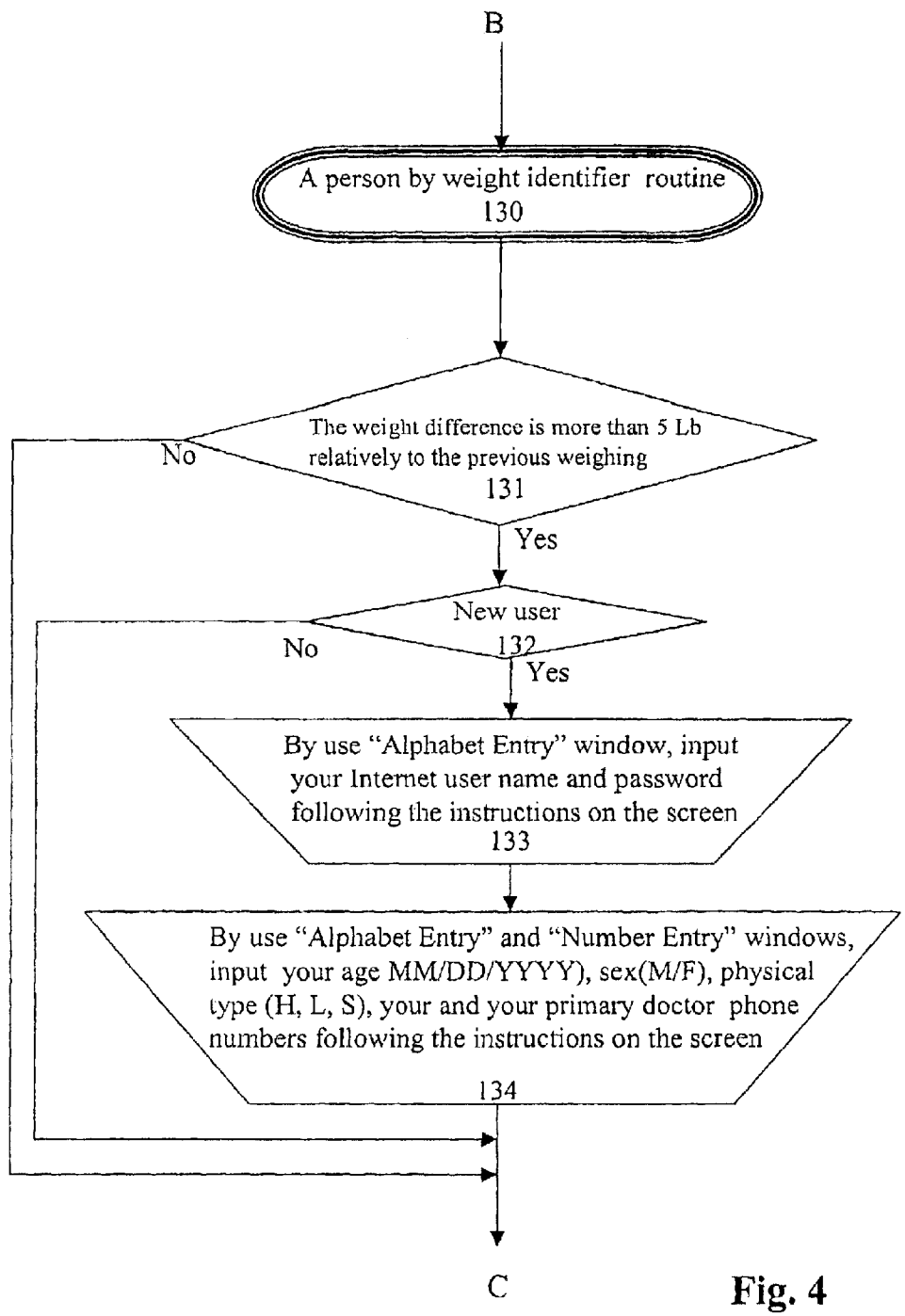
FIG. 4 is a flowchart for a person by weight identifier routine.

FIG. 4 shows a patient by weight identifier routine 130, which is also resident upon the microprocessor of the device. In this routine the patient has to input into the hidden overweight preventing system his private information. A patient or operator only needs to enter this information once, namely, the first day that he or she operates the system. Every new measurement after that, a patient by weight identifier routine 130 recognizes owner of the HEWENS by his weight 131. If the weight difference between two consecutive measurements more or less than 5 pounds (or other appropriate weight greater or less than five pounds, which will indicate a different person is on the scale), routine 130 will check if a different person is attempting to use the HEWENS 132.

Figure 6:
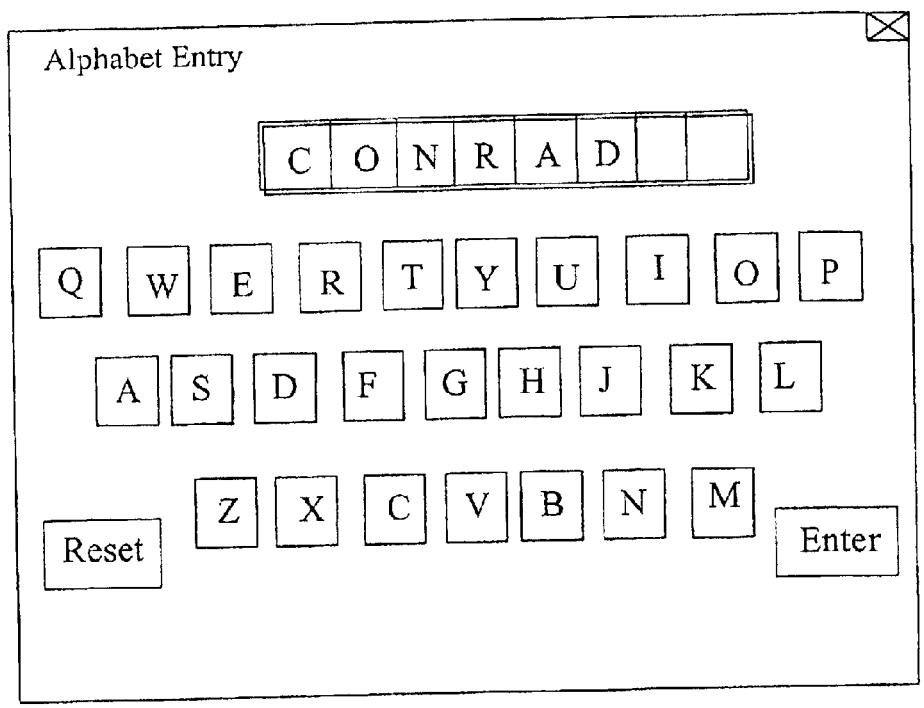
FIG. 6 is an illustration of an alphabetical entry pop-up window.
Figure 7:
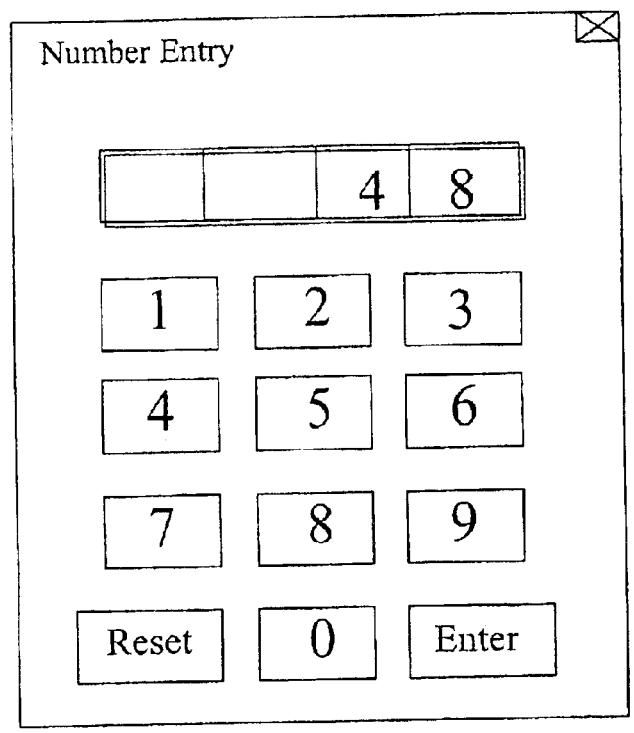
FIG. 7 is an illustration of a display of a number entry pop-up window.

If so, the new person or patient is invited to input there internet name and password 133 by use of the "Alphabet Entry" pop-up window (FIG. 6). If it is determined there is a new user, the system will ask them to input (block 134) their age, sex, physical type. Physical type can be identified as follows: (H=a highly active individual, L=a limitedly active individual and S=a sedentary individual). The user will also be asked to input his/her and a primary doctor's name, address, phone number and other contact information such as e-mail address by use of the "Alphabet Entry" window and "Number Entry" window (FIG. 7). After this initial sequence, the system asks several additional questions, for example, to show or not the result of weighing and measuring of the height on the screen next time.

As an alternative, and when the TOPS system is provided as a subscription service each new user may be asked to pay a subscription fee for example by a credit card, wherein the credit card information is also inputted in the HEWENS device.

Figure 5:
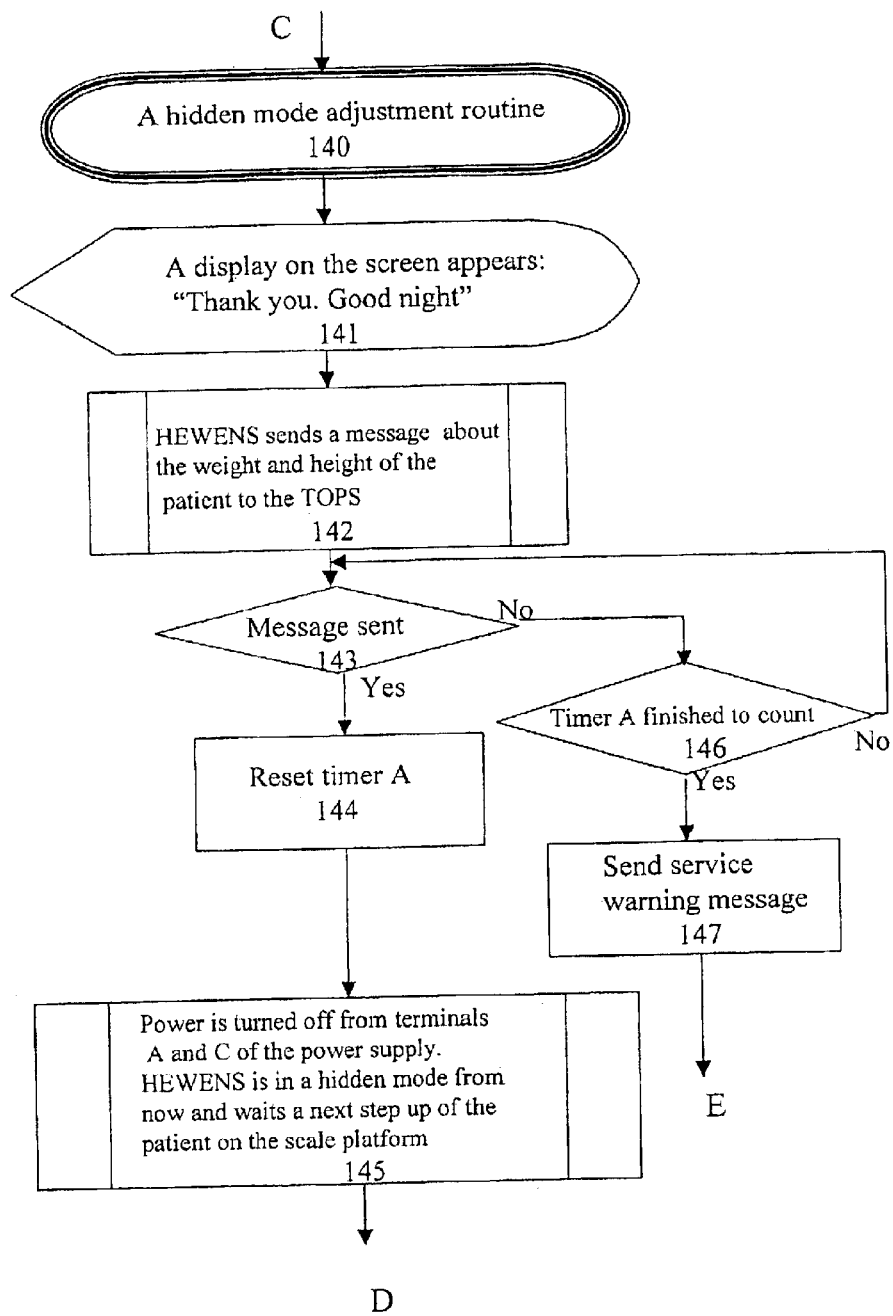
FIG. 5 is a flowchart for a hidden mode adjustment routine.

FIG. 5 shows a hidden mode adjustment routine 140 that is also resident upon the microprocessor of the device. After the HEWENS 80 measures the weight and height of the patient, it arranges a connection with the Internet server of the trend overweight preventing service (TOPS) to supply the new data. The screen "Thank you. Good night" appears (block 141). At this point HEWENS 80 sends the results (block 142) of both of the weight and height measurements to the client database of the TOPS. After HEWENS 80 sends the message (block 143), it resets timer A (block 144). Microcontroller 81 checks the output of timer A that creates a time interval of 30 minutes. When timer A was reset (block 144), control unit 85 of the microcontroller 81 turns off the output voltage (block 145) on the terminals A and C of the power supply 95. Terminals A and C supply the power for the touch screen display 88, modem 89, analog-to-digital converter (ADC) 93 and interface unit 94 of the power-controlled scale 90, and power-controlled height measuring device 96.

At this point, the height and weight news sender (HEWENS) 80 starts to work in a hidden mode and only its microcontroller 81 and weighing platform 91 and operational amplifier circuit 92 of the power-controlled scale 90 will have voltage supply from the terminal B of the power supply 95. The HEWENS 80 shows that it is in a hidden mode and all is ok by blinking a green light emitting diode 87. The HEWENS 80 uses less power in a hidden mode than in a regular one and will stay in this economical mode till a patient will step up on the weighing platform 91 of power-controlled scale 90 on the next night or weighing interval. If the message is not able to be sent due to communications problems within or after 30 minutes (block 143), timer A finishes its count, the timer's output becomes active (block 146), and HEWENS 80 sends a service warning message (block 147). When a patient steps on the weighing platform 91 the second night or weighing interval, operational amplifier circuit 92 of the power-controlled scale 90 will create a signal that the control unit 85 will see and it will accordingly turn on the output voltage on terminal A.

Output voltage on terminal C of the power supply 95 will be turned off because the height and weight news sender 80 measures the height just once a month. Simultaneously, control unit 85 triggers multi-channel timer 84, channel A of which will count since this night a time interval for example 2 minutes for a weight measurement. After the scale measures the patient's weight (less than 1 minute), the HEWENS unit will establish an internet connection with the internet server and client database of the trend overweight preventing service (TOPS). The TOPS system will receive this data by a message from HEWENS 80. The voltage will be turned off from terminal A in 2 minutes and HEWENS 80 will go into the hidden mode again.

The HEWENS devices also monitor the number of weight measurements per month. If there are less than 10 measurements during a month, the HEWENS device will show on the touch screen display 88 a warning to the patient that the accuracy of the overweight predicting model may not be accurate.

Figure 8:
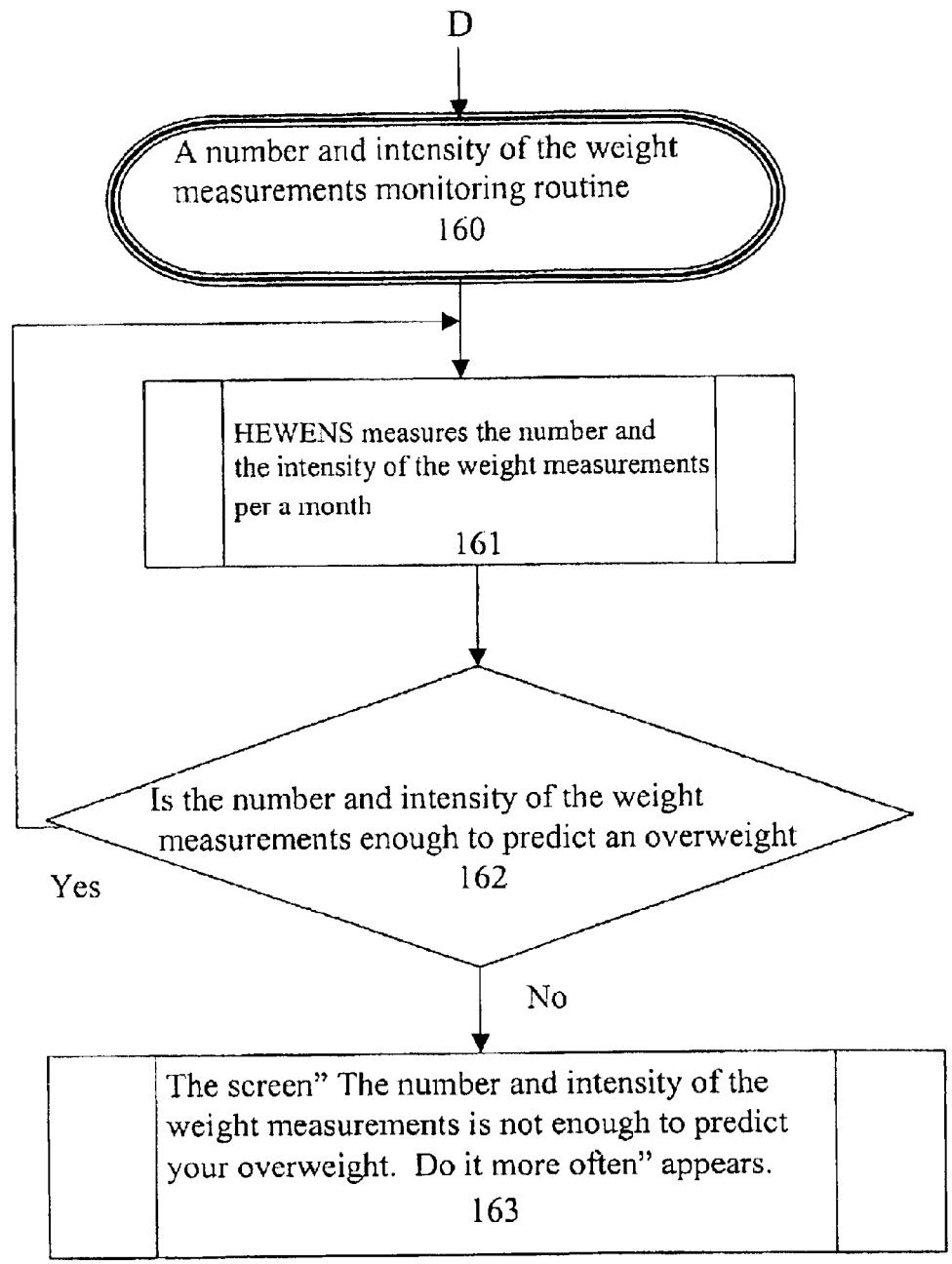
FIGS. 8–10 illustrate a flow chart for the weight measurement monitoring routine.

FIG. 8 shows a number and intensity of the weight measurements monitoring routine 160 of the HEWENS device that one uses to realize that number and intensity of the weight measurements are enough to successfully predict an overweight trend or lack thereof for the user. For this purpose, HEWENS measures the number and the intensity of the weight measurements per month (block 161) and checks (block 162) if the number and intensity of the weight measurements are enough to predict a possible overweight trend as well as errors. If the number and the intensity of the weight measurements are not enough to predict an overweight condition or lack thereof, HEWENS shows a warning (block 163) on the touch screen display 88. Alternatively, the number and intensity of the weight measurements monitoring routine 160 is run at the TOPS instead of the HEWENS device and the information is then provided to the individual's doctor as the HEWENS device operates in a non-dialog mode.

Figure 9:
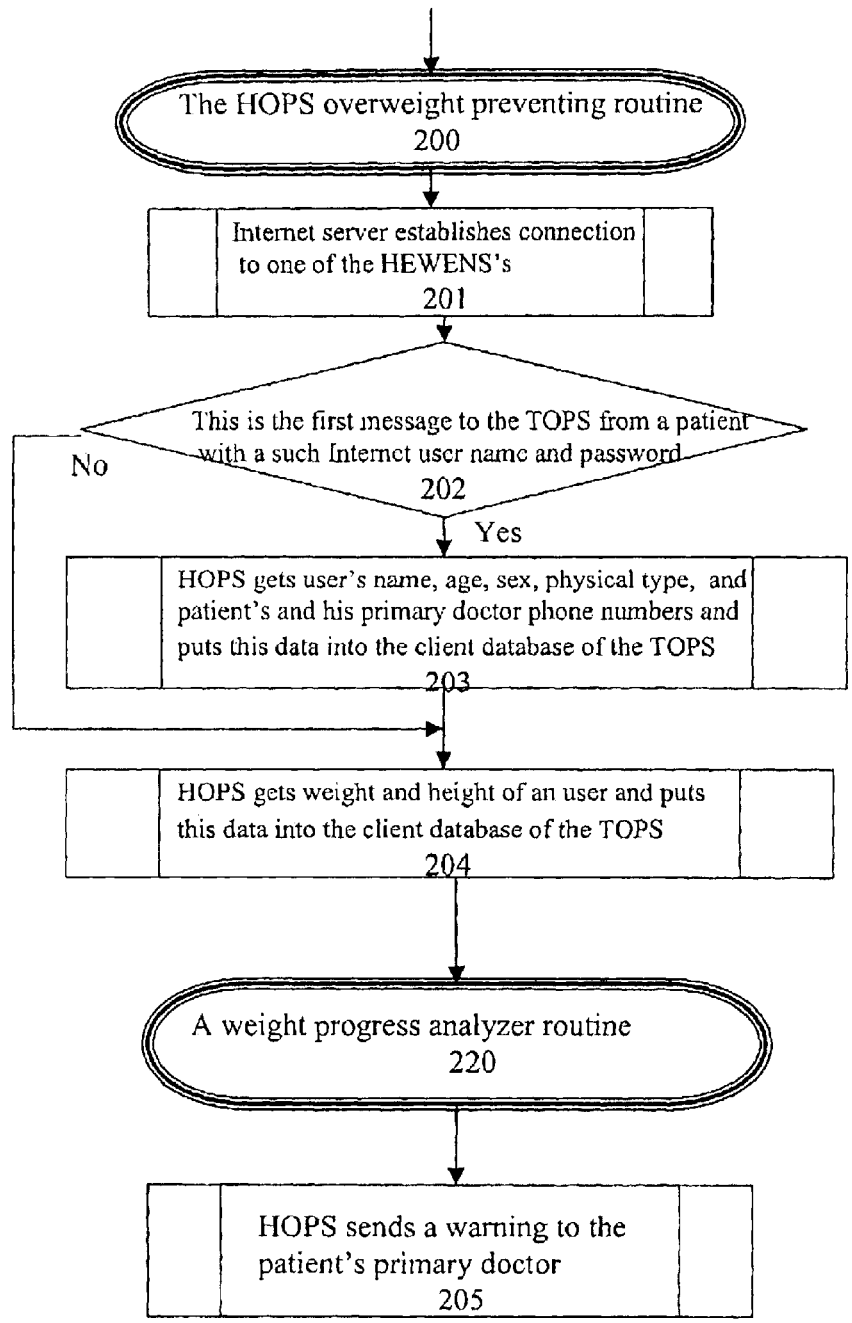

FIG. 9 shows the HOPS overweight preventing routine 200 for interacting with the HEWENS devices. After internet server establishes a connection 201 to one of the HEWENS 80 devices, through the hidden mode operation of routine 140, TOPS recognizes (block 202) if this connection is the first for this patient. During the first internet session 204, HOPS gets a weight of a patient and puts his data into a client database of the TOPS. The data is retrieved from the HEWENS device via the Internet connection. In case the current internet session is the first one with this patient (block 203), HOPS also receives and inputs the new user's name, age, height, sex, physical type, and contact information of the patient and his primary doctor's contact information.

Figure 10:
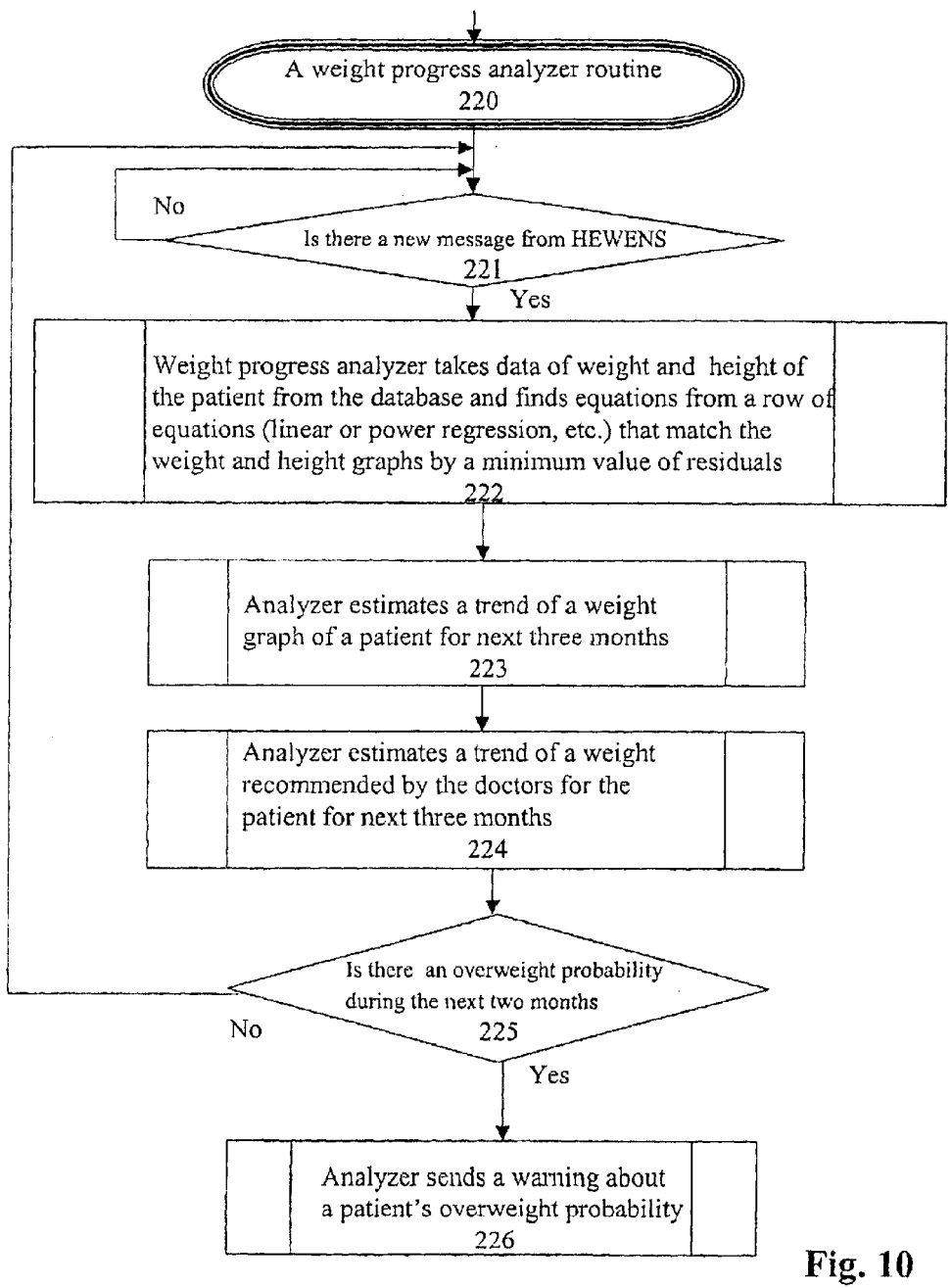

In every day work, HOPS uses a weight progress analyzer routine 220 (FIG. 10). After HEWENS sends each new message 221 consisting of a weight and if applicable height data to the TOPS system, weight progress analyzer takes data of weight and height of each patient from the TOPS database and finds equations from a row of equations (linear or power regression, etc.) that match the weight and height graphs by a minimum value of residuals (block 222). After that, a weight progress analyzer 15 estimates a trend of a weight graph of each patient for the next three months (block 223) and a trend of a weight recommended by the patient's doctor for the next three months (block 224). If there is an overweight probability during the next two months (block 225), analyzer sends a warning about a patient's overweight probability (block 226). After that, HOPS sends a warning by the phone to the patient's primary doctor (block 205) about a patient's overweight probability during the next two months. Of course, the periods mentioned above (e.g., months) may be greater or less than the aforementioned values.

In addition, HEWENS device 80 also has a correction feature wherein inaccurate weight readings are discarded, which may be due to the individual's movement on the scale prior to the reading being recorded. In this feature the reading is discarded if it is outside a prescribed parameter or alternatively a message or prompt may be made available to the individual through the touch screen requesting a re-weighing. If the result is again outside the prescribed parameter the device may inquire as whether a new person is on the scale (routine 130).

Figure 11:
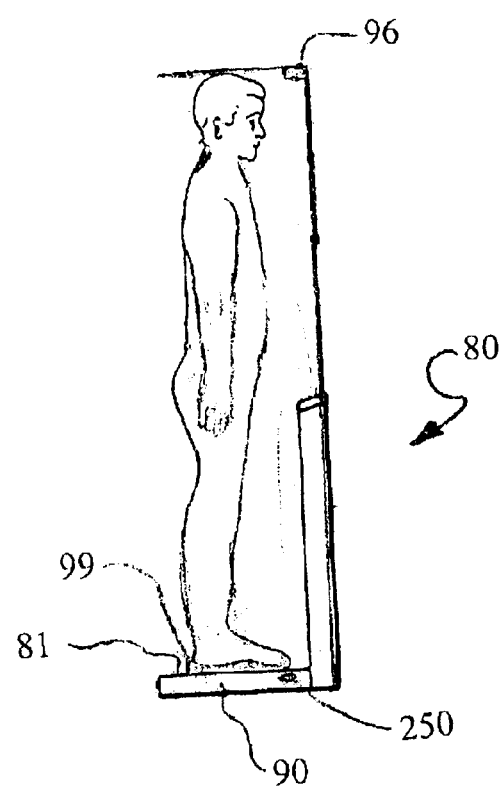
FIG. 11 is an illustration of an individual on a one-way automatic data transmission device of the present disclosure.

FIG. 11 illustrates an individual stepping on a platform 99 of HEWENS device 80. It is noted that the device illustrated in FIG. 11 is just one example of HEWENS device 80. For example the power controlled height measuring device can be either mechanical, optical, a combination of both or equivalent structures of the aforementioned. The HEWENS device can be battery powered or provided with power from a typical outlet connection. In addition, modem 89 is contemplated as being phone, DSL, cable, wireless, radio frequency (RF, with a corresponding emitter and collector for emitting and receiving the RF signals), infrared (IR, with a corresponding emitter and collector for emitting and receiving IR signals) or equivalents thereof, wherein the data in non-dialog mode is transferred to the Trend Overweight Preventing Service (TOPS) for use in the Hidden Overweight Preventing System (HOPS). For example a wireless data port 250 is disposed on a surface of the HEWENS device.

Thus, the present disclosure provides a hidden overweight preventing and one-way long term system and method that will, without any efforts of the people being monitored, except for stepping on the scale, predict an overweight trend or lack thereof. Since the system operates in a one-way non-dialog transmission mode the individual is unaware of their possible trend towards an overweight condition unit they are contacted by their doctor who is part of the HOPS network. In addition, and since the system is also available with a non-screen read out of the user's weight the user may be more inclined to use the HEWENS, device as they do not have to see their weight reading and they will not know if they are trending towards an overweight condition unless they are contacted by their doctor or primary physician.

In addition, and as yet another alternative, the HOPS system is configured with children's height and weight charts according to age in the weight progress analyzer and the information provided by the HEWENS device is used not only to predict an overweight trend in a child but whether the child's height and weight are progressing within standard parameters for age and sex. Thus, and in this embodiment the HOPS system will also notify the child's doctor if the child is trending out of standard growth charts. In addition, the system will also be able to determine if there has been an abrupt change in the child's growth pattern (e.g., significant weight loss, gain, etc.) Again, this information will be provided in a non-dialog format wherein the HEWENS device only supplies the data and the child or parent is only contacted by the doctor if a trend is detected by the system. Also, all of the feature of the previously mentioned embodiments are available in the child monitoring system.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for preventing obesity in an individual comprising:
    monitoring an individual's weight by periodically supplying in non-dialog mode the weight and height reading to a preventing system, said preventing system receiving the weight and height reading through a device that is adapted to collect and send data corresponding to the weight and height reading through an internet connection;
    analyzing weight and height reading and determining if the individual's weight profile has changed; and
    providing feedback to the individual's primary doctor, the feedback will indicate whether the individual is trending towards an overweight condition, wherein a weight progress analyzer estimates a trend of a weight graph of the individual for the next three months and compares it to a trend of a weight recommended for the individual and if there is an overweight probability during the next two months, the weight progress analyzer sends a warning to the individual's doctor about a patient's overweight probability during the next two months.

2. The method for preventing obesity in an individual as in claim 1, wherein said device starts to send the height and weight reading in a hidden mode automatically upon receipt of an input to said device.

3. The method for preventing obesity in an individual as in claim 2, wherein said hidden mode is activated by an individual stepping on said device.

4. The method for preventing obesity in an individual as in claim 1, wherein the step of providing feedback to the individual further comprises allowing the individual to choose a diet plan and exercises from a plurality of diet plans and exercises in the memory of a personal computer that can be connected to the preventing system.

5. The method for preventing obesity in an individual as in claim 1, wherein the individual is a child and the weight and height readings are used with an age reading to determine whether the child is trending within predetermined growth charts or there has been a significant change in the trend of the child's growth chart or curve.

6. A remote weight and height reading apparatus configured for providing one way data communication with an overweight preventing system for interpreting received data, comprising:

a scale being configured to power up a data input and data output device upon receipt of a load of an individual, said data input and said data output devices being adapted to be coupled to said scale, said data input device comprising means to store data in a transferable format, said data output device being adapted to transfer data only via electronic means to a system device adapted to receive and store the transferred data and said system device being adapted to analyze the transferred data and provide a signal indicative of an overweight trend;

wherein said scale powers up said data input and data output device only after an individual has stepped on a platform of said apparatus; and means for determining whether a prescribed period of time has elapsed since said individual has stepped off of said scale.

7. The apparatus and system as in claim 6, wherein said system device is adapted to provide said signal to an individual's primary doctor who has been inputted into said data input device by said individual.

8. The apparatus and system as in claim 6, further comprising means for obtaining the height of said individual and sending corresponding data into said data output device.

9. The apparatus and system as in claim 8, further comprising means for determining whether a prescribed period of time has elapsed since the height of said individual has been measured.

10. The apparatus and system as in claim 6, further comprising means for determining whether a different individual has stepped onto said scale.

11. The apparatus and system as in claim 6, further comprising means for determining whether data corresponding to said individual should be sent to said system device.

12. The apparatus and system as in claim 6, wherein said system device comprises a means for predicting an overweight trend in said individual.

13. The apparatus and system as in claim 12, wherein said system device is adapted to receive data only from a plurality of remote weight and height reading apparatus.

14. The apparatus and system as in claim 13, wherein said electronic means is a modem and internet connection system adapted to automatically transfer data from only the remote weight and height reading apparatus to the system device.

15. The apparatus and system as in claim 12, wherein said means for predicting an overweight trend in said individual utilizes data received from said data output device.

16. The apparatus and system as in claim 6, further comprising a touch screen for data entry by said individual.

17. A remote weight and height reading apparatus configured for providing one way data communication with an overweight preventing system for interpreting received data, comprising:

a scale being configured to power up a data input and data output device upon receipt of a load of an individual, said data input and said data output devices being adapted to be coupled to said scale, said data input device comprising means to store data in a transferable format, said data output device being adapted to transfer data only via electronic means to a system device adapted to receive and store the transferred data and said system device being adapted to analyze the transferred data and provide a signal indicative of an overweight trend;

wherein said scale powers up said data input and data output device only after an individual has stepped on a platform of said apparatus; and a touch screen for data entry by said individual, wherein said device allows the individual to set up an option to show or not the result of current weighing of the individual on the screen.

18. The apparatus and system as in claim 17, further comprising a liquid crystal display for providing interactive messages to said individual from the remote weight and height reading apparatus only.

19. A method for preventing obesity in a group of individuals comprising:

monitoring each individual's weight by periodically supplying in non-dialog mode the weight and height reading to a preventing system, said preventing system receiving the weight and height reading through a device that is adapted to collect and send data corresponding to the weight and height reading through an internet connection; and analyzing weight and height reading of each individual and determining if any of the individual's weight profile has changed; and providing feedback to the primary doctor of the individual whose weight profile has changed, the feedback will indicate whether the individual is trending towards an overweight condition, wherein a weight progress analyzer estimates a trend of a weight graph of each individual for the next three months and compares it to a trend of a weight recommended for the individual and if there is an overweight probability during the next two months, the weight progress analyzer sends a warning to the individual's doctor about a patient's overweight probability during the next two months.

* * * * *